(12) United States Patent
Topgaard et al.

(10) Patent No.: US 11,112,476 B2
(45) Date of Patent: Sep. 7, 2021

(54) METHOD OF EXTRACTING INFORMATION ABOUT A SAMPLE BY NUCLEAR MAGNETIC RESONANCE MEASUREMENTS

(71) Applicant: CR Development AB, Lund (SE)

(72) Inventors: Daniel Topgaard, Lund (SE); Samo Lasic, Lund (SE)

(73) Assignee: CR Development AB

( * ) Notice: Subject to any disclaimer, the term of this patent is extended or adjusted under 35 U.S.C. 154(b) by 0 days.

(21) Appl. No.: 16/065,086

(22) PCT Filed: Dec. 22, 2016

(86) PCT No.: PCT/SE2016/051311
§ 371 (c)(1),
(2) Date: Jun. 21, 2018

(87) PCT Pub. No.: WO2017/116300
PCT Pub. Date: Jul. 6, 2017

(65) Prior Publication Data
US 2019/0011519 A1     Jan. 10, 2019

(30) Foreign Application Priority Data
Dec. 29, 2015 (SE) .................................. 1551719-6

(51) Int. Cl.
*G01R 33/54* (2006.01)
*G01N 24/08* (2006.01)
(Continued)

(52) U.S. Cl.
CPC ............ *G01R 33/543* (2013.01); *A61B 5/055* (2013.01); *G01N 24/08* (2013.01); *G01R 33/448* (2013.01);
(Continued)

(58) Field of Classification Search
None
See application file for complete search history.

(56) References Cited

U.S. PATENT DOCUMENTS 5,212,447 A    5/1993   Paltiel
5,696,448 A   12/1997   Coates et al.
(Continued)

FOREIGN PATENT DOCUMENTS

CN    104574298 A    4/2015
JP    H07-151715 A   6/1995
(Continued)

OTHER PUBLICATIONS

Callaghan et al: "Diffusion-relaxation correlation in simple pore structures", Journal of Magnetic Resonance, Jun. 2003, vol. 162, nr.2, p. 320-327.
(Continued)

*Primary Examiner* — Douglas X Rodriguez
(74) *Attorney, Agent, or Firm* — Condo Roccia Koptiw LLP

(57) ABSTRACT

According to an aspect of the present inventive concept, there is provided a method of extracting information about a sample, the method comprising: performing a plurality of magnetic resonance measurements on the sample, each measurement including subjecting the sample to an encoding sequence, at least a part of the sequence being adapted to encode a magnetic resonance signal attenuation due to nuclear relaxation and diffusion, wherein at least one parameter of a gradient pulse sequence is varied between at least a subset of said plurality of measurements, and at least one measurement of said subset includes a gradient pulse sequence having a diffusion-encoding tensor representation with more than one non-zero eigenvalue, and wherein at least a subset of said plurality of measurements include encoding for different levels of magnetic resonance signal
(Continued)

attenuation due to nuclear relaxation; and extracting information about the sample from signals resulting from said plurality of magnetic resonance measurements, the information including nuclear relaxation and diffusion characteristics for the sample.

16 Claims, 9 Drawing Sheets

(51) Int. Cl.
    *G01R 33/44*         (2006.01)
    *G01R 33/563*       (2006.01)
    *A61B 5/055*        (2006.01)
    *G06F 17/18*        (2006.01)
    *A61B 5/00*         (2006.01)

(52) U.S. Cl.
    CPC ....... *G01R 33/56341* (2013.01); *G06F 17/18* (2013.01); *A61B 5/4064* (2013.01); *A61B 2576/026* (2013.01); *G01N 24/081* (2013.01)

(56) References Cited

U.S. PATENT DOCUMENTS

| | | | |
|---|---|---|---|
| 6,133,735 | A | 10/2000 | Hurlimann et al. |
| 6,369,567 | B1 | 4/2002 | Song et al. |
| 6,462,542 | B1 | 10/2002 | Venkataramanan et al. |
| 6,570,382 | B1 | 5/2003 | Hurlimann et al. |
| 6,597,171 | B2 | 7/2003 | Hurlimann et al. |
| 6,850,060 | B2 | 2/2005 | Song et al. |
| 6,891,369 | B2 | 5/2005 | Hurlimann et al. |
| 7,852,077 | B2 | 12/2010 | Song et al. |
| 7,894,891 | B2 | 2/2011 | Song et al. |
| 9,052,409 | B2 | 6/2015 | Prange et al. |
| 9,995,812 | B2 | 6/2018 | Topgaard et al. |
| 2003/0178994 | A1 | 9/2003 | Hurlimann et al. |
| 2004/0189296 | A1 | 9/2004 | Sun et al. |
| 2005/0270023 | A1 | 12/2005 | Freedman |
| 2011/0234220 | A1 | 9/2011 | Mitchell et al. |
| 2012/0038673 | A1* | 2/2012 | Iwata ................ A61B 5/055 345/649 |
| 2012/0112743 | A1 | 5/2012 | Granlund et al. |
| 2013/0057277 | A1 | 3/2013 | Zielinski et al. |
| 2015/0153433 | A1* | 6/2015 | Paulsen ............. G01N 24/081 324/309 |
| 2017/0261584 | A1* | 9/2017 | James ............... G01R 33/5601 |

FOREIGN PATENT DOCUMENTS

| | | |
|---|---|---|
| JP | 2009-524830 A | 7/2009 |
| JP | 2014-195532 A | 10/2014 |
| JP | 2015-123305 A | 7/2015 |
| JP | 2015-518568 A | 7/2015 |
| WO | 2015/042416 A1 | 3/2015 |
| WO | WO 2015/119569 A1 | 8/2015 |

OTHER PUBLICATIONS

Bernin et al: "NMR diffusion and relaxation correlation methods: New insights in heterogeneous materials", Current Opinion in Colloid and Interface Science, Jun. 2013, vol. 18, nr.3, p. 166-172.
Topgaard: "Isotropic diffusion weighting using a triple-stimulated echo pulse sequence with bipolar gradient pulse paiirs", Microporous and Mesoporous Materials, Mar. 2015, vol. 205, p. 48-51.
Basser et al., "Diffusion Tensor MRI: Theory, Experimental Design and Data Analysis", John Wiley & Sons, Ltd., NMR in Biomedicine, vol. 15, 2002, pp. 456-467.
Basser et al., "MR Diffusion Tensor Spectroscopy and Imaging", Biophysical Journal vol. 66, Jan. 1994, pp. 259-267.
Blinc et al., "Anisotropy of Self-Diffusion in the Smectic-A and Smecti-C Phases", Physical Review Letters, vol. 33, No. 20, Nov. 11, 1974, pp. 1192-1195.
Callaghan et al., "Diffusion-Diffusion Correlation and Exchange as a Signature for Local Order and Dynamics", Journal of Chemical Physics, vol. 120, No. 8, Feb. 22, 2004, pp. 4032-4038.
Callaghan, Paul T., "Multidimensional PGSE NMR", Translational Dynamics and Magnetic Resonance, First Edition, Oxford University Press, 2011, pp. 397-407.
Cory et al., "Applications of Spin Transport as a Probe of Local Geometry", Code 6122, Chemistry Division, Naval Research Laboratory, 1990, pp. 149-150.
Cory et al., "Multiple Scattering by NMR", Journal of the American Chemical Society 121, 1999, pp. 7935-7936.
Efron, Bradley, "Nonparametric Estimates of Standard Error: The Jackknife, the Bootstrap and Other Methods", Biometrika vol. 68, No. 3, 1981, pp. 589-599.
Eriksson et al., "Isotropic Diffusion Weighting in PGSE NMR by Magic-Angle Spinning of the Q-Vector", Journal of Magnetic Resonance 226, 2013, pp. 13-18.
Eriksson et al., "NMR Diffusion-Encoding with Axial Symmetry and Variable Anisotropy: Distinguishing Between Prolate and Oblate Microscopic Diffusion Tensors with Unknown Orientation Distribution", The Journal of Chemical Physics, vol. 142, AIP Publishing, 2015, pp. 104201.1-104201.11.
Finsterbusch, Jurgen, "Multiple Wave Vector Diffusion Weighted NMR", Annual Reports on NMR Spectroscopy vol. 72, 2011, pp. 225-299.
Gerstner et al., "Diffusion and Diffusion Tensor Imaging in Brain Cancer", Seminars in Radiation Oncology-Journal-Elsevier, vol. 21, No. 2, Apr. 2011, pp. 141-146.
Hofling et al., "Diffusion Tensor Imaging Detects Axonal Injury and Demyelination in the Spinal Cord and Cranial Nerves of a Murine Model of Globoid Cell Leukodystrophy", NMR in Biomedicine, vol. 22, No. 10, Dec. 2009, pp. 1100-1106.
Holmberg et al., "Phase Behaviour of Concentrated Surfactant System", John Wiley & Sons, Ltd., Surfactants and Polymers in Aqueous Solution, 1998, pp. 67-96.
Lasic et al., "Microanisotropy Imaging: Quantification of Microscopic Diffusion Anisotropy and Orientational Order Parameter by Diffusion MRI with Magic-Angle Spinning of the Q-Vector", Original Research, vol. 2, Article 11, Feb. 2014, 14 pages.
Lawson et al., "Solving Least Squares Problems", Classics in Applied Mathematics, Society for Industrial and Applied Mathematics, 1974, pp. 05-08.
Leemans et al., "Diffusion Tensor Imaging and Beyond", Wiley-Liss, Inc., Imaging Methodology—Review, Magnetic Resonance in Medicine, vol. 65, 2011, pp. 1532-1556.
Martins et al., "Two-Dimensional Correlation of Isotropic and Directional Diffusion Using NMR", Physical Review Letters, vol. 116, Feb. 26, 2016, pp. 087601-1-087601-6.
Mitra, Partha P., "Multiple Wave-Vector Extensions of the NMR Pulsed-Field-Gradient Spin-Echo Diffusion Measurement", The American Physical Society, Physical Review B, vol. 51, No. 21, Jun. 1, 1995, pp. 15074-15078.
Mori et al., "Diffusion Weighting by the Trace of the Diffusion Tensor within a Single Scan", Magnetic Resonance in Medicine vol. 33, No. 1, 1995, pp. 41-52.
Mori et al., "Fiber Tracking: Principle and Strategies—A Technical Review", John Wiley & Sons, Ltd., NMR in Biomedicine, vol. 15, 2002, pp. 468-480.
Price, William, "Double PGSE and Multi-Dimensional Correlations", NMR Studies of Translational Motion: Principles and Applications, 2009, pp. 272-281.
Shemesh et al., "Conventions and Nomenclature for Double Diffusion Encoding NMR and MRI", Magnetic Resonance in Medicine, vol. 75, 2016, pp. 82-87.
Shemesh et al., "Detecting Diffusion-Diffraction Patterns in Size Distribution Phantoms Using Double-Pulsed Field Gradient NMR: Theory and Experiments", The Journal of Chemical Physics, vol. 132, 2010, pp. 034703-1-034703-12.
Sjolund et al., "Constrained Optimization of Gradient Waveforms for Generalized Diffusion Encoding", Journal of Magnetic Resonance, vol. 261, 2015, pp. 157-168.

(56) References Cited

OTHER PUBLICATIONS

Stejskal, E O., "Use of Spin Echoes in a Pulsed Magnetic Field Gradient to Study Anisotropic, Restricted Diffusion and Flow", The Journal of Chemical Physics, vol. 43, No. 10, 1965, pp. 3597-3603.
Szczepankiewicz et al., "Quantification of Microscopic Diffusion Anisotropy Disentangles Effects of Orientation Dispersion from Microstructure: Applications in Healthy Volunteers and in Brain Tumors", NeuroImage, vol. 104, 2015, pp. 241-252.
Topgaard, Daniel, "Isotropic Diffusion Weighting in PGSE NMR: Numerical Optimization of the Q-MAS PGSE Sequence", Microporous and Mesoporous Materials, vol. 178, 2013, pp. 60-63.
Torrey, H. C., "Bloch Equations with Diffusion Teriris", Physical Review, vol. 104, No. 3, Nov. 1, 1956, pp. 563-565.
Tournier et al., "Direct Estimation of the Fiber Orientation Density Function from Diffusion-Weighted MRI Data Using Spherical Deconvolution", NeuroImage vol. 23, No. 3, 2004, pp. 1176-1185.
Westin et al., "Measurement Tensors in Diffusion MRI: Generalizing the Concept of Diffusion Encoding", Medical Image Computing and Computer-Assisted Intervention vol. 17, No. 03, 2014, pp. 209-216.
Whittall et al., "Quantitative Interpretation of NMR Relaxation Data", Journal of Magnetic Resonance, vol. 84, 1989, pp. 134-152.
De Santis S., et al. "Resolving Myelin and Axonal Properties within the Same Voxel in Presence of Crossing Fibers by Combing Inversion Recovery and Diffusion Acquisitions", Proceedings of the International Society for Magnetic Resonance in Medicine, vol. 22, 103, Apr. 25, 2014.
CN 104574298 A, Cited in Office Action dated Dec. 1, 2020, in related Chinese Patent Application No. 201680077398.6.
JP 2014-195532 A, Cited in Office Action dated Dec. 1, 2020, in related Chinese Patent Application No. 201680077398.6.
JP 2015-123305 A, Cited in Office Action dated Dec. 1, 2020, in related Chinese Patent Application No. 201680077398.6.
JP H07-151715 A, English Language Counterpart U.S. Pat. No. 5,212,447 A.
JP 2009-524830 A, English Language Counterpart U.S. Pat. No. 7,894,891 B1 (Previously cited in Information Disclosure Statement filed on Sep. 17, 2020 in the above-identified U.S. Appl. No. 16/065,086).
JP 2015-518568 A, English Language Counterpart U.S. Pat. No. 9,995,812 B2.

\* cited by examiner

METHOD OF EXTRACTING INFORMATION ABOUT A SAMPLE BY NUCLEAR MAGNETIC RESONANCE MEASUREMENTS

CROSS REFERENCE TO RELATED APPLICATIONS

This application is the National Stage Entry under 35 U.S.C. § 371 of Patent Cooperation Treaty Application No. PCT/SE2016/051311, filed 22 Dec. 2016, which claims priority from Sweden Application No. 1551719-6, filed 29 Dec. 2015, the contents of which are hereby incorporated by reference herein.

TECHNICAL FIELD

The present inventive concept relates to a method of extracting information about a sample by nuclear magnetic resonance measurements.

BACKGROUND

Nuclear magnetic resonance (NMR) methods have a unique ability to non-invasively characterize the properties of liquids in heterogeneous porous materials as diverse as rocks, wood, and brain tissue. NMR observables such as offset frequency, longitudinal relaxation rate $R_1$, and transverse relaxation rate $R_2$, depend on the chemical composition of the pore liquid and interactions between the pore liquid and the porous matrix. Through application of magnetic field gradients, the phase and amplitude of the NMR signal can be encoded with information about the spatial position and translational motion of the pore liquids,[1,2] the latter often separated into the self-diffusion coefficient D and the flow velocity v. The spatial information forms the foundation for magnetic resonance imaging (MRI).

The presence of multiple microscopic environments for the pore liquid gives rise to distributions rather than unique values of the NMR observables. Substantial differences in the observables are required to reliably separate the signal contributions from distinct populations of pore liquids.[3]

Anisotropic porous structures give rise to corresponding anisotropy of the translational motion of the pore liquid. The directional dependence of the observed value of D is captured in the diffusion tensor D,[4] which can be quantified by performing a series of measurements with varying directions of the applied magnetic field gradients.[5,6] The diffusion tensor imaging[6,7] (DTI) version of MRI makes it possible to follow the paths of the nerve fibers throughout the living human brain,[8] as well as to detect pathological conditions such as tumors[9] and demyelination.[10] For simple pore geometries, the observed shape and orientation of D can be related to the underlying pore structure with relative ease. Interpretational ambiguities arise when the investigated volume element comprises multiple environments with different anisotropy and/or orientations. Even for randomly oriented materials, which are isotropic on the macroscopic scale, diffusion encoding in a series of discrete[11-17] or continuously varying directions[18-22] can be used to prove the presence of microscopic diffusion anisotropy and quantify its magnitude, e.g., as the microscopic fractional anisotropy $\mu FA$[20,23] or the diffusion anisotropy parameter $D_A$.[24] Through appropriately designed acquisition protocols and analysis methods, it is now possible to disentangle the effects of microscopic anisotropy and pore orientations,[20] as well as to separately characterize the anisotropy of components with distinct values of the isotropic diffusivity $D_{iso}$.[25] The results of these experiments can be reported as the 2D distribution $P(D_{iso}, D_A)$. With knowledge of the microscopic anisotropy, the pore orientations can be quantified as a 2D orientation distribution function $P(\theta, \phi)$,[26] where $\theta$ and $\phi$ are, respectively, the polar and azimuthal angles in the laboratory frame of reference.

Despite these recent advances in characterizing heterogeneous anisotropic materials, data analysis may be challenging for instance when the components have similar values of $D_{iso}$ or $D_A$.

SUMMARY

An objective of the present inventive concept is to provide a method of extracting information about a sample which enables an improved resolving power in terms of probing properties of diffusing components of the sample. Further or alternative objectives may be understood from the following.

According to an aspect of the present inventive concept, there is provided a method of extracting information about a sample, the method comprising:

performing a plurality of magnetic resonance measurements on the sample, each measurement including subjecting the sample to an encoding sequence, at least a part of the sequence being adapted to encode a magnetic resonance signal attenuation due to nuclear relaxation and diffusion, wherein at least one parameter of a gradient pulse sequence of an encoding sequence is varied between at least a subset of said plurality of measurements, and at least one measurement of said subset includes a gradient pulse sequence having a diffusion-encoding tensor representation with more than one non-zero eigenvalue, and wherein at least a subset of said plurality of measurements include encoding for different levels of magnetic resonance signal attenuation due to nuclear relaxation; and extracting information about the sample from signals resulting from said plurality of magnetic resonance measurements, the information including nuclear relaxation and diffusion characteristics for the sample The present inventive concept is based on the insight that prior art protocols enabling characterization of heterogeneous anisotropic materials may be augmented by measurements encoding for different levels (i.e. different degrees) of magnetic resonance signal attenuation due to nuclear relaxation. Thereby, diffusion characteristics may be correlated with characteristics of the nuclear relaxation of the nuclear spin system within the sample. The method hence provides a means of resolving nuclear relaxation characteristics of diffusion components in the sample. This may be achieved even in the presence of only subtle differences in the isotropic or anisotropic diffusion of the components. Thus, the ability to characterize or distinguish properties of diffusing components may be improved.

A component may refer to a component of the sample with a distinct diffusion characteristic, such as a distinct isotropic and/or anisotropic diffusivity.

A diffusion-encoding tensor representation of a gradient pulse sequence may also be referred to as a diffusion-encoding tensor representation b of a magnetic gradient pulse sequence G of a magnetic resonance measurement (e.g. a tensor representation $b_i$ of a gradient pulse sequence $G_i$ of a magnetic resonance measurement i), b being given by $$b = \int_0^{\tau_E} q(t) q^T(t)\, dt,$$

where q(t) is a time-dependent dephasing vector (which is proportional to $$\int_0^t G(t')dt'\right)$$

and $t_E$ is the time of echo formation. Accordingly, the gradient pulse sequence of the at least one measurement of said subset may be generated such that the diffusion encoding tensor representation b of said gradient pulse sequence presents more than one non-zero eigenvalue.

The at least a subset of the plurality of measurements wherein at least one parameter of a gradient pulse sequence is varied, and including at least one measurement including a gradient pulse sequence having a diffusion-encoding tensor representation with more than one non-zero eigenvalue, may be referred to as a first subset of the plurality of measurements.

The at least a subset of the plurality of measurements including encoding for different levels of magnetic resonance signal attenuation due to nuclear relaxation may be referred to as a second subset of the plurality of measurements.

The first subset and the second subset may be completely overlapping (i.e. wherein the first and the second subset may refer to the same subset), partially overlapping or non-overlapping.

Accordingly, each one of said plurality of magnetic resonance measurements may be performed using a respective combination of a diffusion encoding and a nuclear relaxation encoding. The parameters of the encoding sequence controlling the encoding of the magnetic resonance signal attenuation due to nuclear relaxation and diffusion may be referred to as a set of acquisition parameters. At least a subset of said plurality of magnetic resonance measurements may be performed using different sets of acquisition parameters.

According to one embodiment said at least one parameter of a gradient pulse sequence is varied between measurements (e.g. of the first subset) to provide different diffusion encoding in the sample. Said at least one parameter of a gradient pulse sequence may be varied between measurements to encode for different levels of signal attenuation. At least one or a combination of: a modulation of a gradient pulse sequence, a maximum gradient amplitude, and/or an orientation of the diffusion encoding may be varied between measurements.

According to one embodiment at least a subset of the plurality of measurements (e.g. the second subset) include encoding for different levels of signal attenuation due to transverse relaxation and/or longitudinal relaxation.

According to one embodiment extracting the information includes estimating a representation of a probability distribution indicating a probability to find a particular combination of nuclear relaxation characteristics and diffusion characteristics in the sample.

The probability distribution may thus indicate an estimate (e.g. as a number between 0 and 1) of the probability or likelihood that a particular combination of nuclear relaxation characteristics and diffusion characteristics exists in the sample.

The probability distribution may indicate a respective probability for each one of a plurality of different combinations of nuclear relaxation characteristics and diffusion characteristics.

A combination of nuclear relaxation characteristics and diffusion characteristics may include a combination of: a longitudinal and/or a transverse relaxation rate, and one or more of: an isotropic diffusion, an anisotropic diffusion and an orientation of a diffusion tensor.

The probability distribution may be estimated based on an equation relating echo signals resulting from said plurality of measurements to a kernel and the probability distribution, wherein the components of the kernel are based on an acquisition parameter and a diffusion or a relaxation characteristic. The probability distribution may be estimated by determining a solution to the equation. The equation may relate the signals resulting from said plurality of measurements to a product of the kernel and the probability distribution.

The nuclear relaxation characteristics and the diffusion characteristics may be estimated using the probability distribution.

The nuclear relaxation characteristics of the extracted information may include an estimate of a transverse relaxation rate and/or a longitudinal relaxation rate. The extracted information may include, for each component of the sample, a respective estimate of a transverse relaxation rate and/or a longitudinal relaxation rate.

The diffusion characteristics of the extracted information may include an estimate of an isotropic diffusivity. The diffusion characteristics of the extracted information may include, for each component of the sample, a respective estimate of an isotropic diffusivity.

The diffusion characteristics of the extracted information may include an estimate of an anisotropic diffusivity. The diffusion characteristics of the extracted information may include, for each component of the sample, a respective estimate of an anisotropic diffusivity.

The diffusion characteristics of the extracted information may include an estimate of an orientation of a diffusion tensor D representing diffusion for a component in the sample. The diffusion characteristics of the extracted information may include, for each component of the sample, a respective estimate of an orientation of a diffusion tensor D representing diffusion for said component.

The diffusion characteristics of the extracted information may include estimates of the elements of a diffusion tensor D representing diffusion for a component in the sample. The diffusion characteristics of the extracted information may include, for each component in the sample, estimates of the elements of a diffusion tensor D representing diffusion for said component.

According to one embodiment at least a part of the encoding sequence of each measurement is adapted to further encode a phase variation of the magnetic resonance signal due to a flow in the sample.

The method may further comprise extracting information about the sample including flow characteristics.

The nuclear relaxation characteristics, the diffusion characteristics and/or the flow characteristics of the extracted information may be used to generate contrast in an MRI image of the sample.

BRIEF DESCRIPTION OF THE DRAWINGS

The above, as well as additional objects, features and advantages of the present inventive concept, will be better understood through the following illustrative and non-limiting detailed description of preferred embodiments of the present inventive concept, with reference to the appended drawings.

DETAILED DESCRIPTION OF PREFERRED EMBODIMENTS

To facilitate understanding of the present inventive concept, a discussion of some theoretical concepts will now be provided with reference to the drawings.

Theory

Figures 1A, 1B:
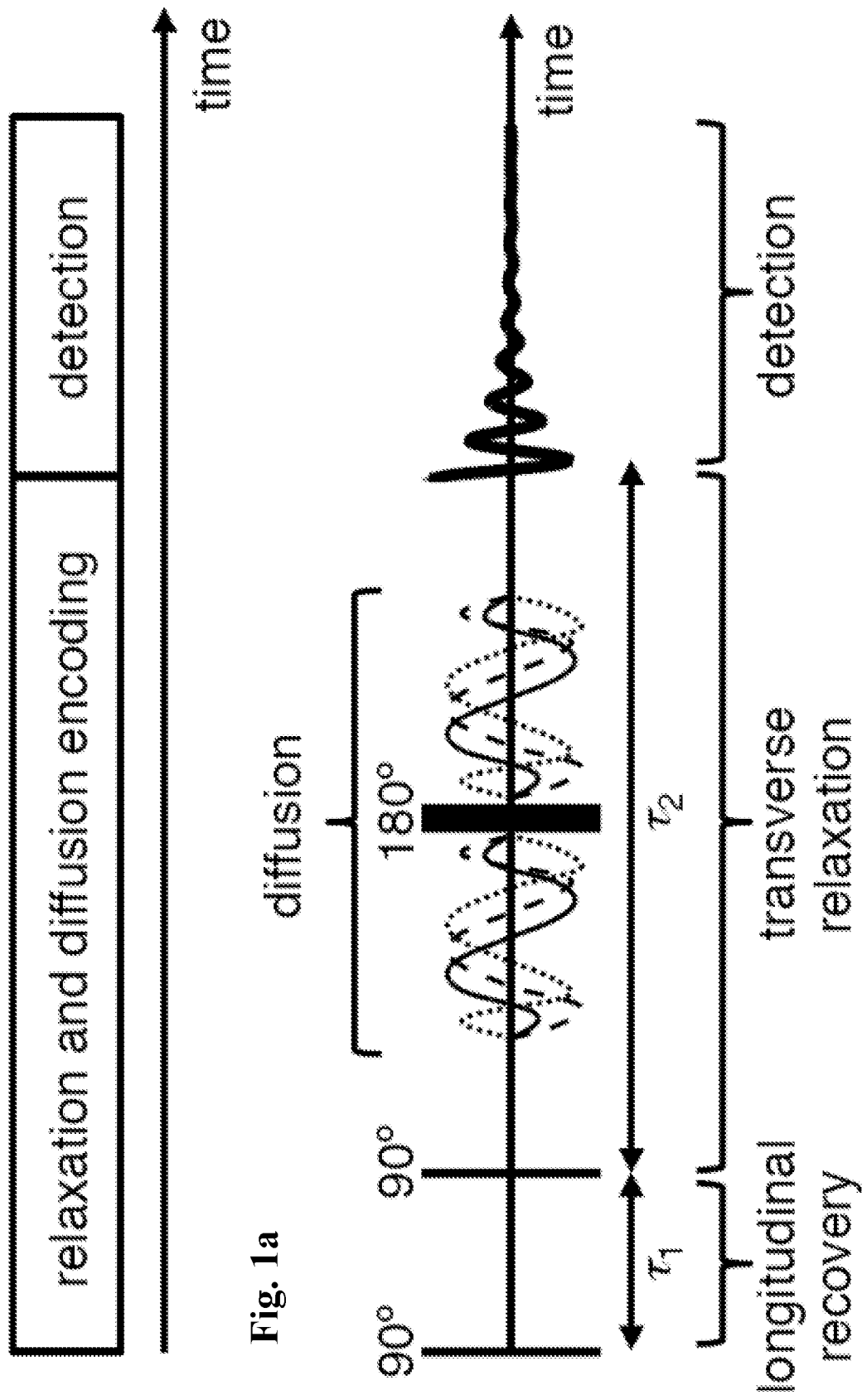
FIG. 1 schematically illustrates an example of an NMR measurement sequence.

Relaxation and diffusion NMR experiments are usually performed with pulse sequences comprising a block with relaxation and diffusion encoding preceding a block with signal detection as illustrated with the general pulse sequence in FIG. 1a and a specific implementation in FIG. 1b. Accordingly, FIG. 1a shows an "encoding block" which modulates the NMR signal according to the values of the relaxation rates and the diffusion tensor, and a "detection block" where the NMR signal is read out (e.g. as a spectrum or an image). FIG. 1b illustrates an NMR pulse sequence with 90° and 180° radiofrequency pulses (narrow and broad vertical lines), modulated gradients in three orthogonal directions (solid, dashed, and dotted lines), and detected signal (thick solid line). The signal is modulated by longitudinal recovery, transverse relaxation, and diffusion by the factors, respectively, $[1-\exp(-\tau_1 R_1)]$, $\exp(-\tau_2 R_2)$, and $\exp(-b:D)$ as will be described in detail in the following:

Starting from an initial state with complex transverse magnetization $m_{xy}$ equal to zero, the first 90° RF pulse flips the longitudinal magnetization $m_z$ into the transverse plane. During the time-delay with duration $\tau_1$, the longitudinal magnetization recovers towards the thermal equilibrium value $m_0$ with the longitudinal relaxation rate $R_1$. The second 90° pulse flips the recovered magnetization into the transverse plane where it decays towards zero with the transverse relaxation rate $R_2$ for a time period $\tau_2$ before it is detected. During the $\tau_2$ period, a time-dependent magnetic field gradient $G(t)=[G_x(t)\ G_y(t)\ G_z(t)]^T$ is applied. For a homogeneous anisotropic medium, the evolution of the local magnetization density is given by the Bloch-Torrey equation:[27,1,2]

$$\frac{\partial m_{xy}(r,t)}{\partial t} = [-i\gamma G(t)\cdot r - R_2 + \nabla\cdot D\cdot\nabla]m_{xy}(r,t) \quad (1)$$

and $$\frac{\partial m_z(r,t)}{\partial t} = -R_1[m_z(r,t)-m_0] + \nabla\cdot D\cdot\nabla m_z(r,t). \quad (2)$$

In Eqs. (1) and (2), D is the diffusion tensor. The magnetization at the beginning of the detection period can be obtained by integrating Eqs. (1) and (2), yielding $$m_{xy}(r) = m_0[1-\exp(-\tau_0 R_1)]\exp(-\tau_2 R_2)\exp(-b:D) \exp(ia\cdot v). \quad (3)$$

In the derivation of Eq. (3), it has been assumed that, in addition to diffusion, the molecules flow with a velocity v that remains constant throughout the application of the motion-encoding gradients (coherent flow). The encoding for translational motion is split into the velocity-encoding vector a and the diffusion-encoding tensor b.[24] The expression b:D denotes a generalized scalar product, which is written explicitly as[1,2]

$$b:D = \sum_i \sum_j b_{ij} D_{ij}, \quad (4)$$

where $i,j \in \{x,y,z\}$. The tensor b is given by the integral $$b = \int_0^{t_E} q(t)q^T(t)\,dt, \quad (5)$$

where q(t) is the time-dependent dephasing vector $$q(t) = \gamma \int_0^t G(t')\,dt' \quad (6)$$

and $t_E$ is the time of echo formation, i.e. where $q(t_E)=0$. The vector a equals the first moment of the gradient according to $$a = \gamma \int_0^{t_E} tG(t)\,dt. \quad (7)$$

The detected signal S is proportional to the volume integral $$S \propto \int_V m_{xy}(r)\,dr. \quad (8)$$

For a macroscopic heterogeneous sample volume, the signal can be written as an ensemble average of a longitudinal relaxation factor ($\mathfrak{R}_1$), a transverse relaxation factor ($\mathfrak{R}_2$) and a translational motion factor (T), $$S = S_0 \langle \mathfrak{R}_1 \rangle_2 T \mathfrak{R}, \quad (9)$$

where $S_0$ is the signal that would be obtained if the experiment is made insensitive to the relaxation and translational motion effects mentioned above. The signal can be explicitly written as $$S(\tau_1,\tau_2,b,a) = S_0 \langle [1-\exp(-\tau_1 R_1)]\exp(-\tau_2 R_2)\exp(-b:D) \exp(ia\cdot v) \rangle, \quad (10)$$

where $\langle \cdot \rangle$ denotes an ensemble average over microscopic environments with distinct values of $R_1$, $R_2$, D, and v. The initial intensity $S_0$ is the signal that would be obtained when $\tau_1=\infty$, $\tau_2=0$, and all elements of b and a equal zero. In terms of the multidimensional probability distribution, P, the signal can be expressed by $$S(\tau_1,\tau_2,b_{11},b_{12},b_{13},b_{22},b_{23},b_{33},a_1,a_2,a_3) = \quad (11)$$

$$\ldots S_0 \int_0^\infty \int_0^\infty \int_0^\infty \int_0^\infty \int_0^\infty \int_0^\infty \int_0^\infty \int_0^\infty \int_{-\infty}^\infty \int_{-\infty}^\infty \int_{-\infty}^\infty K(\cdots)$$

-continued $$P(\cdots)dD_{11}\ldots,$$
$$dD_{12}dD_{13}dD_{22}dD_{23}dD_{33}dv_1dv_2dv_3dR_1dR_2$$

which is an integral transform where the kernel K( . . . ), given by $$K(\tau_1,\tau_2,b_{11},b_{12},b_{13},b_{22},b_{23},b_{33},a_0,a_2,a_3,\ldots R_1,R_2,D_{11},$$
$$D_{12},D_{13},D_{22},D_{23},D_{33},v_1,v_2,v_3)=[1-\exp(-\tau_1 R_1)]$$
$$\exp(-\tau_2 R_2)\exp(-b{:}D)\exp(ia\cdot v), \quad (11')$$

maps the eleven-dimensional (11D) probability distribution $P(R_1,R_2,D_{11}, D_{12}, D_{13}, D_{22}, D_{23}, D_{33},v_1, v_2,v_3)$ to the 11D signal. Note that by varying the elements of the velocity-encoding vector a and the diffusion-encoding tensor b the 3 independent velocity component and the 6 independent diffusion tensor components can be measured. Eqs. (11) and (11') reflect the fact that the entangled information about the diffusion tensor size, shape, orientation, the flow velocity and the longitudinal and transverse relaxation rates may, in accordance with the present inventive method, be disentangled by controlling the acquisition parameters and acquiring the multidimensional signal, S, above. Note that the effects of spatially or temporary incoherent flow, the intra voxel incoherent motion (IVIM), are accounted for in the diffusion tensor components above (see Eqs. (11) and (11')). The pulse sequence (FIG. 1) is modified in such way that the experimenter has control of the acquisition parameters in the kernel (11').

In the principal axis system of the b-tensor, the eigenvalues $b_{XX}$, $b_{YY}$, and $b_{ZZ}$ are located on the diagonal while all off-diagonal elements are zero:

$$b = \begin{pmatrix} b_{XX} & 0 & 0 \\ 0 & b_{YY} & 0 \\ 0 & 0 & b_{ZZ} \end{pmatrix}. \quad (12)$$

For simplicity, the following analysis applies to the specific case when both b and D are axisymmetric. When the b-tensor is axisymmetric, then $b_{XX}=b_{YY}$, and it can be written as $$b = \begin{pmatrix} b_\perp & 0 & 0 \\ 0 & b_\perp & 0 \\ 0 & 0 & b_\parallel \end{pmatrix}, \quad (13)$$

where $b_\parallel=b_{ZZ}$ and $b_\perp=b_{XX}=b_{YY}$ are the axial and radial eigenvalues, respectively. While conventional diffusion methods are based on b-tensors with only one non-zero eigenvalue, recent methods for studying microscopic diffusion anisotropy rely on variation of the number of non-zero eigenvalues to encode the signal with information about the magnitudes, shapes, and orientations of diffusion tensors.[18-20,28,24,21,22,17] When the tensor b is axisymmetric, it can be parameterized with the trace b, anisotropy $b_\Delta$, and orientation $(\Theta,\Phi)$.[24] The values of b and $b_\Delta$ are given by the axial and radial eigenvalues, $b_\parallel$ and $b_\perp$, via $$b = 2b_\perp + b_\parallel \quad (14)$$
and $$b_\Delta = \frac{b_\parallel - b_\perp}{b}. \quad (15)$$

Diffusion NMR and MRI methods based on the Stejskal-Tanner pulse sequence are limited to the value $b_\Delta=1$, meaning that $b_\parallel$ is the only non-zero eigenvalue. Isotropic diffusion encoding[29,18] is equivalent to $b_\Delta=0$, implying that all eigenvalues are non-zero and equal: $b_\parallel=b_\perp$.

In analogy with Eqs. (14) and (15), axially symmetric diffusion tensors can be parameterized with the isotropic average $D_{iso}$, anisotropy $D_\Delta$, and orientation $(\theta, \phi)$, which are related to the axial and radial eigenvalues, $D_\parallel$ and $D_\perp$, through[24]

$$D_{iso} = \frac{2D_\perp + D_\parallel}{3} \quad (16)$$

and $$D_\Delta = \frac{D_\parallel - D_\perp}{3D_{iso}}. \quad (17)$$

With this parameterization, the tensor scalar product in Eq. (10) can be conveniently expressed as $$b{:}D = bD_{iso}[1+2b_\Delta D_\Delta P_2(\cos \beta)], \quad (18)$$

where β is the angle between the main symmetry axes of the b and D tensors. Through standard trigonometry, it can be shown that $$\cos \beta = \cos \Theta \cos \theta + \cos(\Phi-\phi)\sin \Theta \sin \theta. \quad (19)$$

The factors following b in Eq. (18) can be interpreted as an effective diffusion coefficient D, which can be explicitly written as $$D = D_{iso}[1+2b_\Delta D_\Delta P_2(\cos \Theta \cos \theta + \cos(\Phi-\phi)\sin \Theta \sin \theta)]. \quad (20)$$

From Eq. (20) it is clear that the diffusivity measured with conventional Stejskal-Tanner methods, with $b_\Delta=1$, is a non-trivial combination of the properties of the b and D tensors.

Assuming that there is no coherent flow, v=0, and that both b and D are axisymmetric, then Eq. (10) can be rewritten as $$S(\tau_1, \tau_2, b, b_\Delta, \Theta, \Phi) = \quad (21)$$
$$S_0 \int_0^\infty \int_0^\infty \int_0^\infty \int_{-1/2}^1 \int_0^\pi \int_0^{2\pi} K(\cdots)P(\cdots)d\phi \sin\theta d\theta dD_\Delta dD_{iso}dR_2 dR_1,$$

which is an integral transform where the kernel K( . . . ), given by $$K(\tau_1,\tau_2,b,b_\Delta,\Theta,\Phi,R_1,R_2,D_{iso},D_\Delta,\theta,\phi)=[1-\exp(-\tau_1 R_1)]$$
$$\exp(-\tau_2 R_2)\exp\{-bD_{iso}[1+2b_\Delta D_\Delta P_2(\cos \Theta \cos \theta + \cos(\Phi-\phi)\sin \Theta \sin \theta)]\}, \quad (22)$$

maps the six-dimensional (6D) probability distribution $P(R_1,R_2,D_{iso},D_\Delta, \theta, \phi)$ to the 6D signal $S(\tau_1, \tau_2,b,b_\Delta, \Theta,\Phi)$. Eqs. (21) and (22) reflect the entangled information about the diffusion tensor size, shape, orientation and the longitudinal and transverse relaxation rates. In accordance with the present inventive method, this information can be disentangled by controlling the acquisition parameters and acquiring the multidimensional signal, S, above. Note that the effects of spatially or temporary incoherent flow are included in the diffusion tensor. The pulse sequence (FIG. 1)

is modified in such way that the experimenter has control of the acquisition parameters in the kernel (22).

The distribution is normalized:

$$\int_0^\infty \int_0^\infty \int_0^\infty \int_{-1/2}^1 \int_0^\pi \int_0^{2\pi} P(R_1, R_2, D_{iso}, D_\Delta, \theta, \varphi) \quad (23)$$

$$d\varphi \sin\theta d\theta dD_\Delta dD_{iso} dR_2 dR_1 = 1.$$

Information about the distribution can be obtained by acquiring signal as a function of $(\tau_1, \tau_2, b, b_\Delta, \Theta, \Phi)$ and inverting Eq. (21). For the purpose of data analysis, Eq. (21) can be recast into matrix form as $$s = Kp, \quad (24)$$

where s is a vector of signals acquired for N different combinations of $(\tau_1, \tau_2, b, b_\Delta, \Theta, \Phi)$, p is a vector of amplitudes of M discrete components $(R_1, R_2, D_{iso}, D_\Delta, \theta, \phi)$, and K is a M×N matrix with elements given by Eq. (22).

When $b_\Delta = 0$, Eq. (18) is reduced to $$b:D = bD_{iso}, \quad (25)$$

which is independent of the diffusion tensor anisotropy $D_\Delta$ and orientation $(\theta,\phi)$.[24] In this case, Eq. (21) can be simplified to $$S(\tau_1, \tau_2, b, b_\Delta = 0) = \quad (26)$$

$$S_0 \int_0^\infty \int_0^\infty \int_0^\infty K(\cdots) P(D_{iso}, R_2, R_1) dD_{iso} dR_2 dR_1,$$

with the kernel K( ... ) now given by $$K(\tau_1, \tau_2, b, b_\Delta = 0, R_1, R_2, D_{iso}) = [1 - \exp(-\tau_1 R_1)] \exp(-\tau_2 R_2) \exp(-b D_{iso}) \quad (27)$$

and where $P(R_1, R_2, D_{iso})$ is the 3D probability distribution of finding a diffusion tensor component with the values $R_1$, $R_2$, and $D_{iso}$.

Acquisition Protocols

Figure 2A:
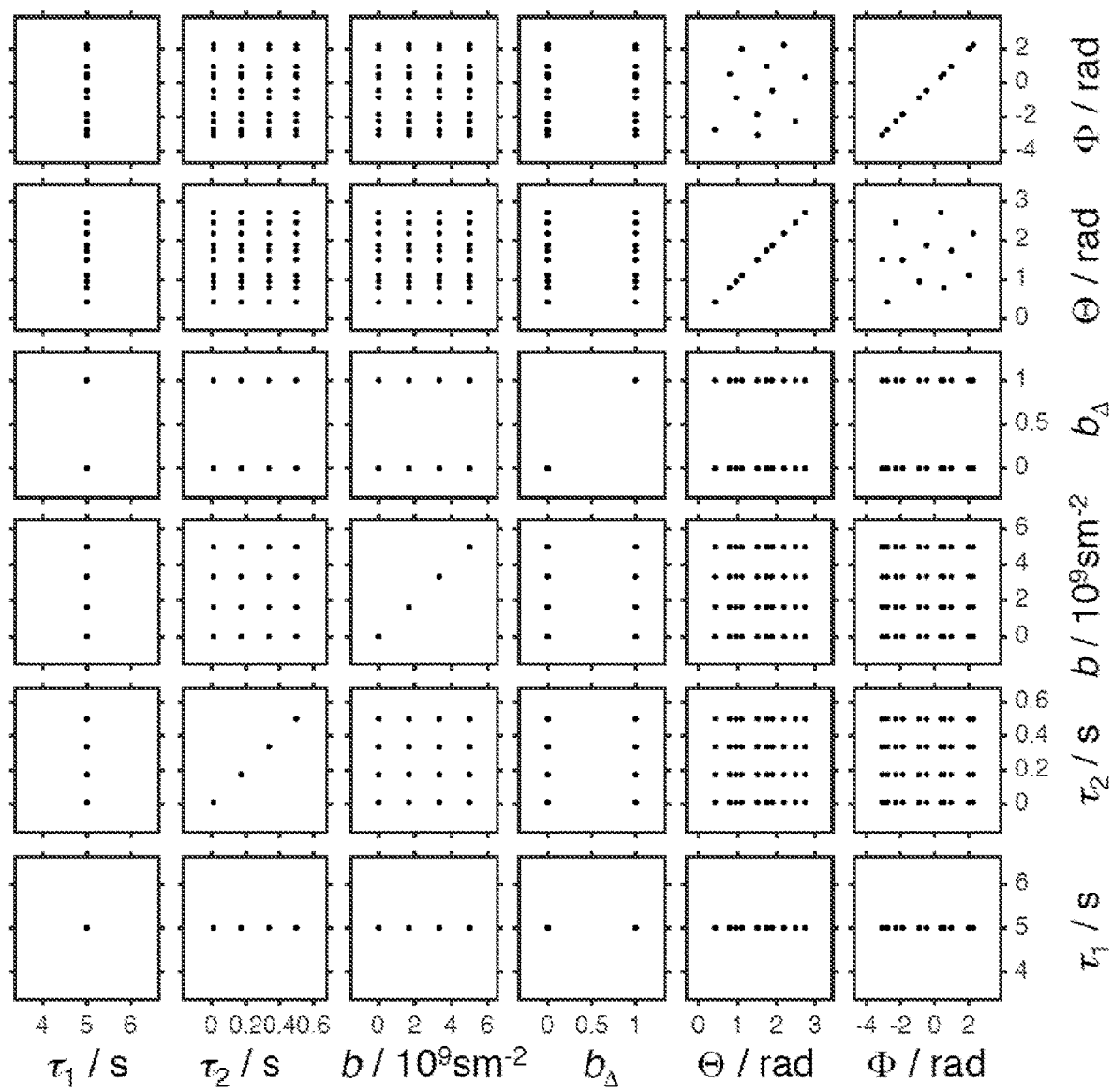
FIG. 2 illustrates examples of acquisition protocols which may be used to extract information about a sample.
Figure 2B:
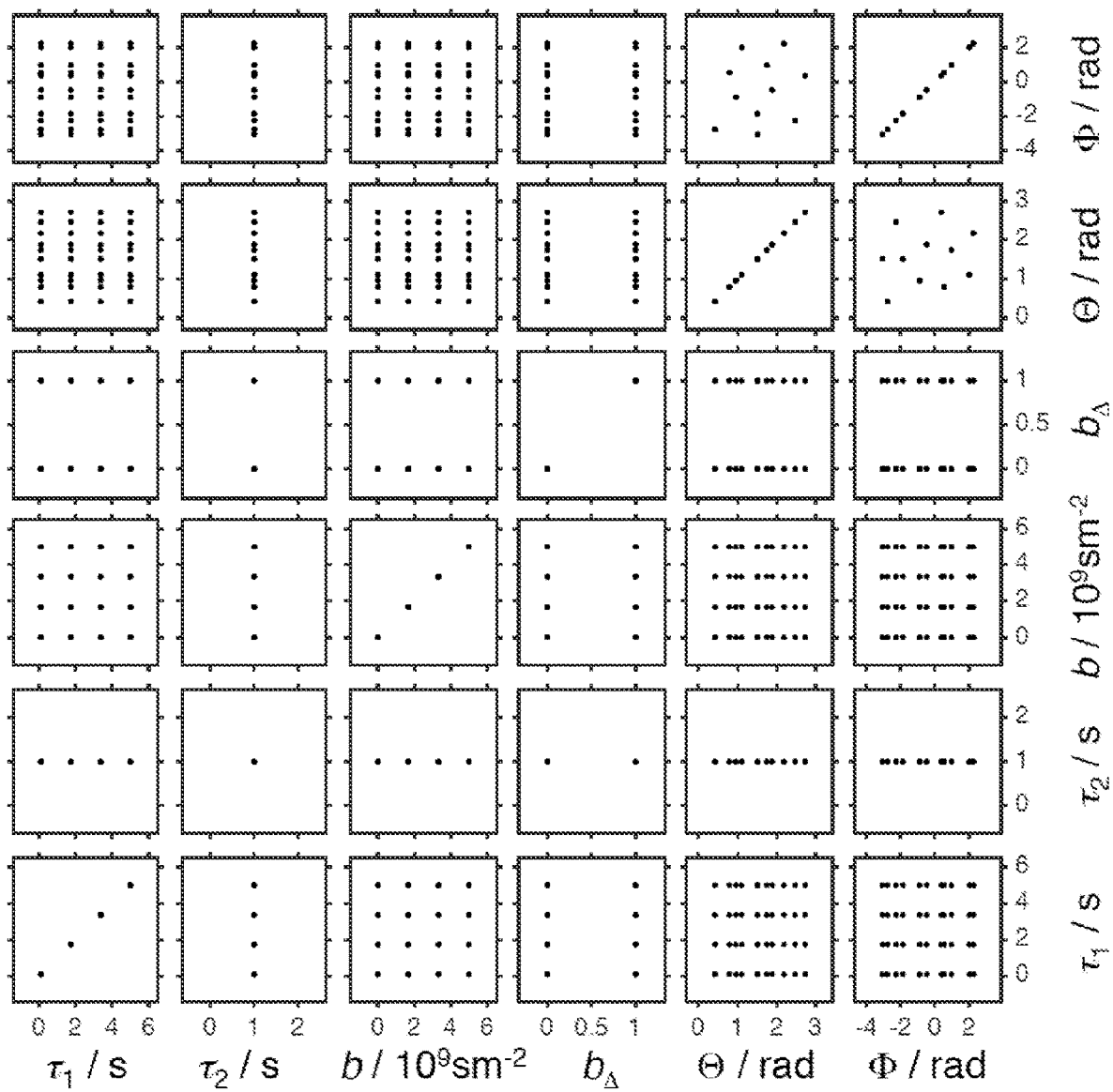
Figure 2C:
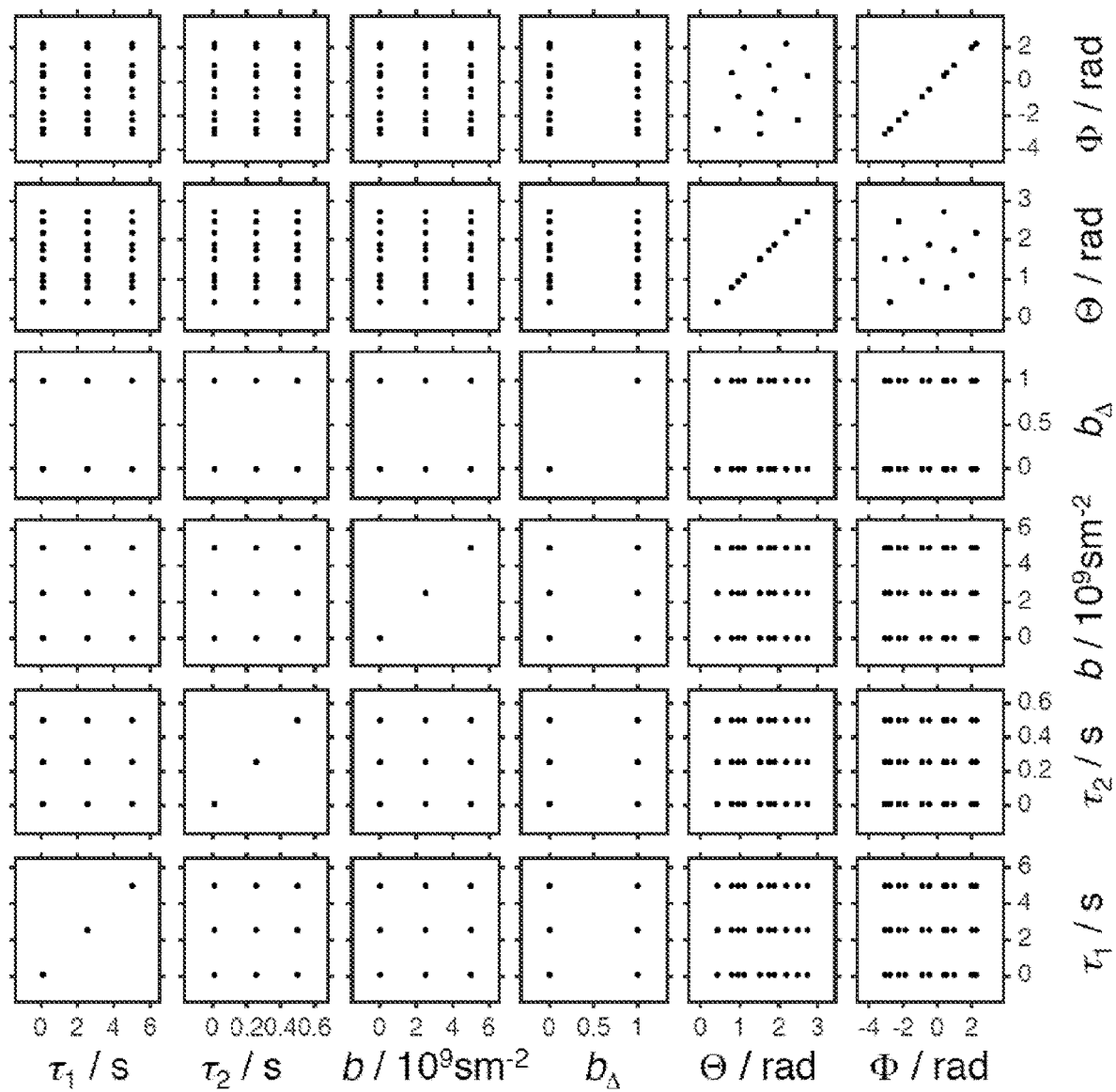
Figure 2D:
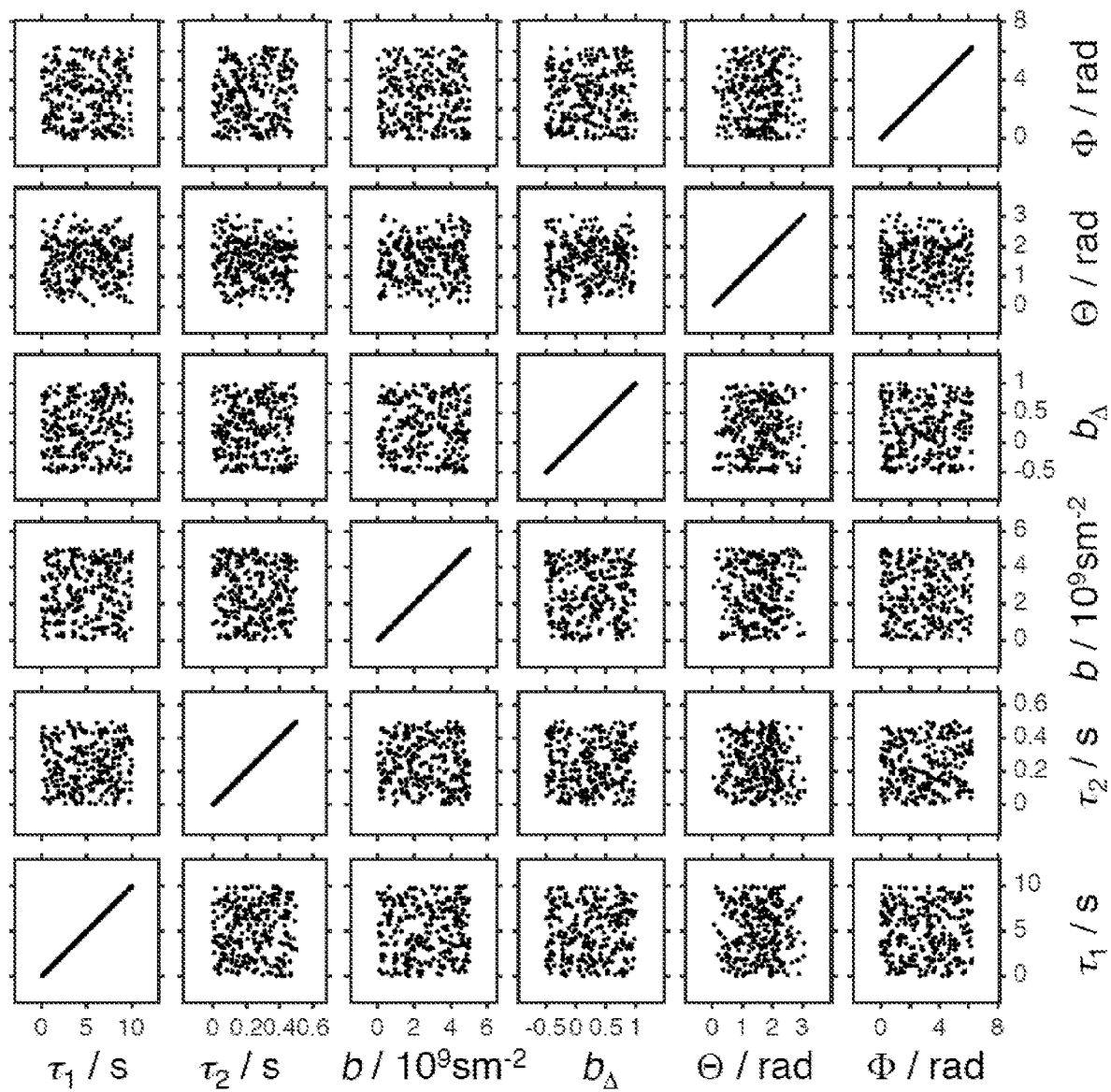

In view of the above, an example measurement series may include measurements with $b_\Delta$ other than unity, as well as sampling of at least one of the time periods $\tau_1$ and $\tau_2$ at more than one value, thereby giving information about the isotropically averaged diffusivity, the diffusion anisotropy, and the nuclear relaxation of the diffusing component(s) and their correlations. Examples of such protocols are displayed in FIG. 2. Generally, the pulse sequences are varied in such way that the acquisition parameters in the kernel (given by equation (22)) may be controlled. In the figures, sampled data points are plotted in all possible 2D projections of the 6D acquisition space with the dimensions longitudinal recovery time $\tau_1$, transverse dephasing time $\tau_2$, magnitude of the b-tensor b, anisotropy of the b-tensor $b_\Delta$, and orientation of the b-tensor $(\Theta, \Phi)$. FIG. 2a enables estimation of a 5D correlation of transverse relaxation rate $R_2$, isotropic diffusivity $D_{iso}$, diffusion tensor anisotropy $D_\Delta$, and diffusion tensor orientation $(\theta,\phi)$. FIG. 2b enables estimation of a 5D correlation of longitudinal relaxation rate $R_1$, isotropic diffusivity $D_{iso}$, diffusion tensor anisotropy $D_\Delta$, and diffusion tensor orientation $(\theta,\phi)$. FIG. 2c enables estimation of a 6D correlation of longitudinal relaxation rate $R_1$, transverse relaxation rate $R_2$, isotropic diffusivity $D_{iso}$, diffusion tensor anisotropy $D_\Delta$, and diffusion tensor orientation $(\theta,\phi)$. FIG. 2d is similar to the FIG. 2c, but implements pseudo-random sampling of the 6D acquisition space. The examples shown in FIGS. 2a and b enables estimation of correlations between the diffusion tensor parameters $(D_{iso}, D_\Delta, \theta, \phi)$ and the relaxation rates $R_1$ or $R_2$, respectively, while the sampling schemes in FIGS. 2c and d enables estimation of the correlations between $(D_{iso}, D_\Delta, \theta, \phi)$ and both of $R_1$ and $R_2$. The 6D acquisition space $(\tau_1, \tau_2, b, b_\Delta, \Theta, \Phi)$ can be sampled with the pulse sequence in FIG. 1b. Other options include the pulse sequence introduced by Topgaard[17] and further modified by Eriksson et al.[24] to allow for continuous sampling of the $b_\Delta$ dimension. By adding an initial 90° pulse and subsequent recovery delay $\tau_1$ to this the Eriksson et al. sequence, full 6D acquisition space becomes accessible. Although these different protocols may provide advantages in different scenarios, it should be noted that, for the inventive idea underlying the general inventive concept, any pulse sequence enabling probing of the acquisition parameter space may be used. Preferably, pulse sequences enabling variation of the acquisition parameters/variables $(\tau_1, \tau_2, b, b_\Delta, \Theta, \Phi)$ between the measurements of the experiment may be used.

If the anisotropy $b_\Delta$ is restricted to $b_\Delta = 1$, it follows from Eq. (20) that an ambiguous result is obtained when $D_\Delta$ is non-zero and the values of $\theta$ and $\phi$ are unknown. If $D_{iso}$ is the main parameter of interest, then it is beneficial to carry out the measurements with $b_\Delta = 0$ where the second term of Eq. (20) becomes zero and the effects of diffusion tensor anisotropy and orientation hence will be absent from the signal S. According to Eqs. (11) and (11'), comprising a more general implementation the present inventive method, information about all the elements of the diffusion tensor D, including tensors without axial symmetry and their orientation in the laboratory frame of reference, the information about flow velocity, the longitudinal and transverse relaxation can be disentangled and correlated.

Example Experiment

In the following, an example of a proof-of-principle experiment will be described as well as the results thereof:

Sample Preparation

A reverse hexagonal lyotropic liquid crystal was prepared by mixing sodium 1,4-bis(2-ethylhexoxy)-1,4-dioxobutane-2-sulfonate (38 wt %) with 2,2,4-trimethylpentane (14 wt %) and water (48 wt %) in a 10 ml vial. After extensive manual mixing and centrifugation to make the mixture homogeneous, 0.5 ml was transferred to a 5 mm NMR tubes. The reverse hexagonal phase is thermodynamically stable at 25° C.,[31] and melts into a reverse micellar phase at elevated temperature. The sample was studied at 29° C. where the reverse hexagonal and reverse micellar phases coexist.

NMR Data Acquisition

Figure 3A:
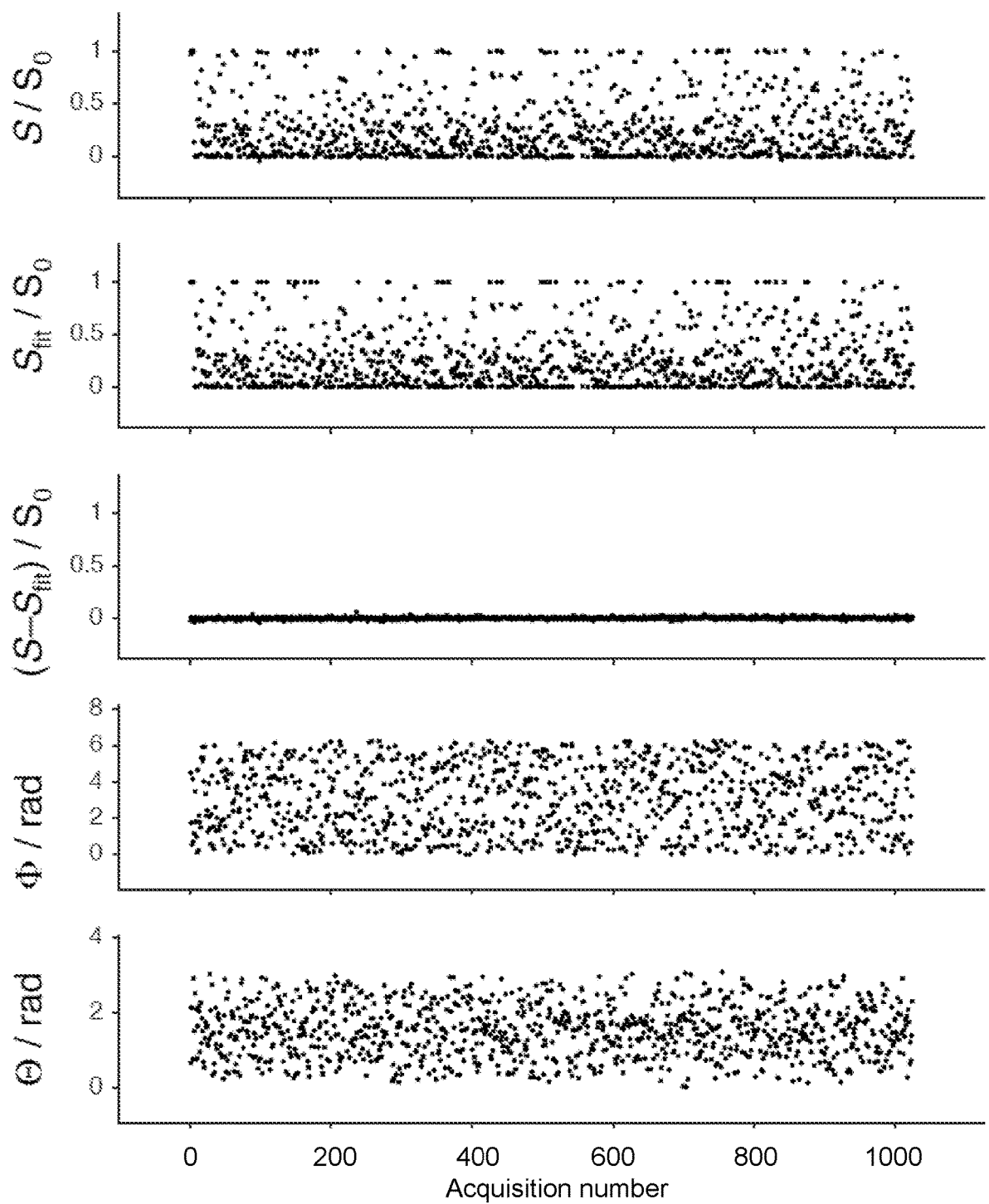
FIG. 3 illustrates an example of a random acquisition protocol which may be used to extract information about a sample and associated experimental results.
Figure 3B:
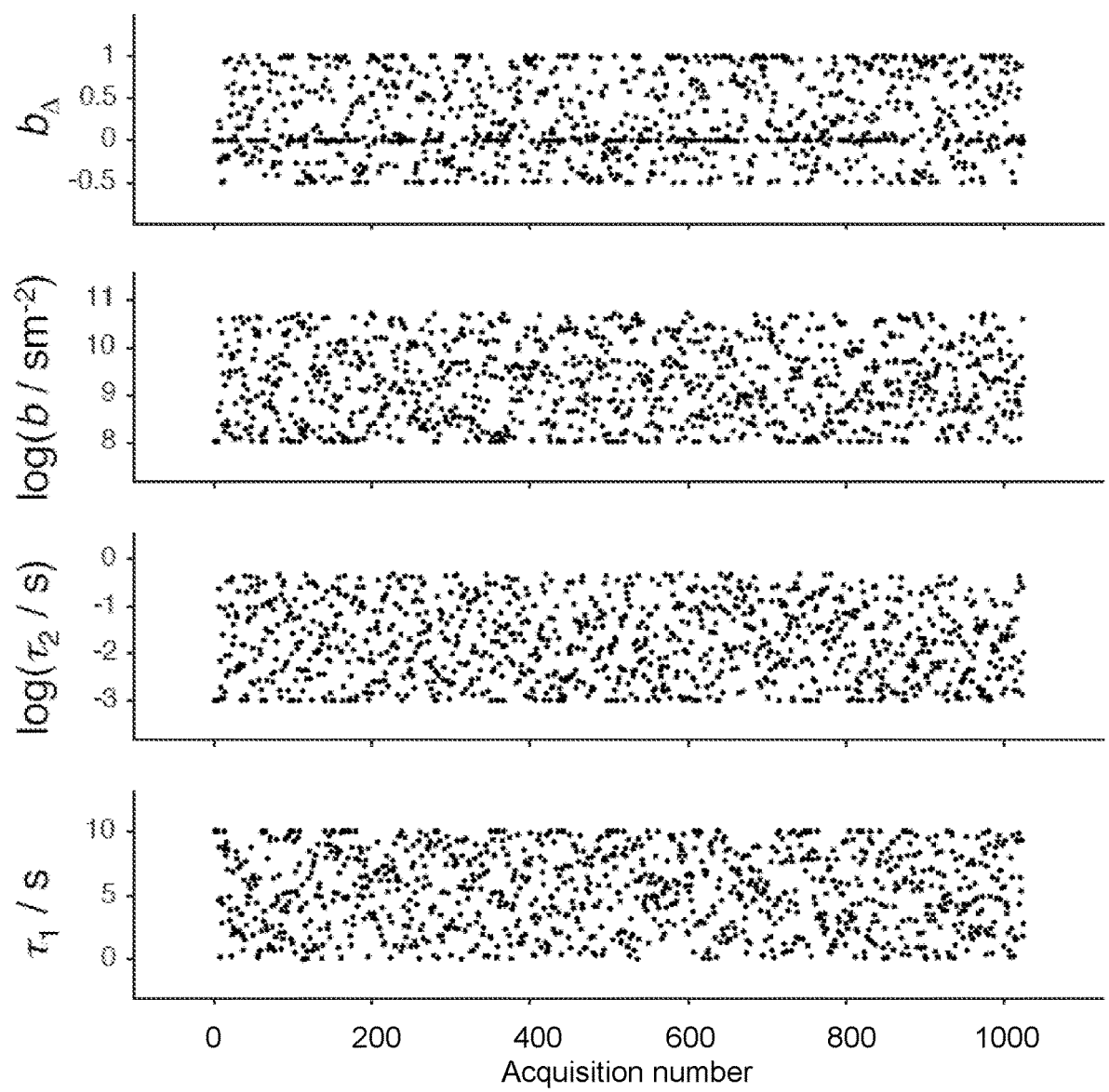

NMR experiments were performed on a Bruker AVII-500 spectrometer operating at 500.13 MHz $^1$H resonance frequency. The spectrometer is equipped with an 11.7 T ultra-shielded magnet fitted with a MIC-5 microimaging probe capable of delivering magnetic field gradients with amplitude 3 T/m in three orthogonal directions. The liquid crystalline sample was studied with a modified version of the triple-stimulated echo pulse sequence introduced by Topgaard[17], here allowing for signal encoding with all of the variables $(\tau_1, \tau_2, b, b_\Delta, \Theta, \Phi)$ as described in the theory section above. The approach of random sampling, as illustrated in FIG. 2d, was used to select 1024 points of the 6D acquisition space. The actual values of the acquisition variables are shown in FIGS. 3a-b. Following the pulse sequence block with relaxation and diffusion encoding, the signal was detected as a free induction decay (FID), giving a high-resolution NMR spectrum upon Fourier transformation. The water resonance line was integrated and stored for further analysis.

Data Analysis and Visualization

The 6D distribution was estimated by numerical inverse integral transform of Eq. (21) using a non negative least squares (NNLS) method[34].

To visualize the discrete components of the six-dimensional (6D) probability distribution $P(R_1,R_2,D_{iso},D_\Delta, \theta,\phi)$, the components were convolved with the Gaussian kernel and mapped to a grid. The selected components of $D_\parallel/D_\perp$ were used to calculate the orientation distribution function (ODF), $P(\theta,\phi)$, which was displayed as spherical mesh with radius scaled by the directionally dependent value of $P(\theta,\phi)$.

A similar procedure may be used when including velocity encoding and encoding for all the diffusion tensor elements according to Eqs. (11) and (11').

Figure 3C:
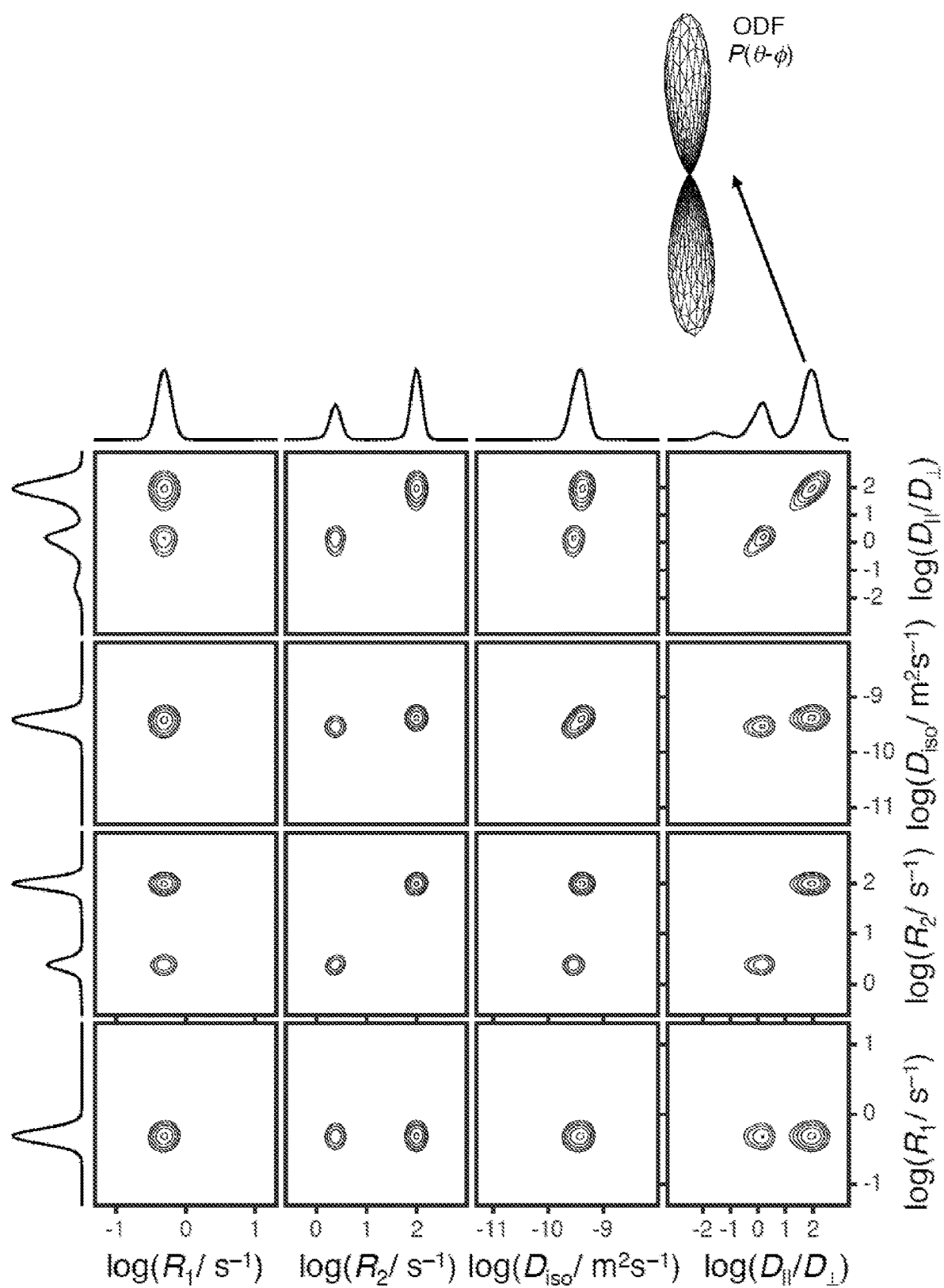

Example for Obtaining Result in FIG. 3(c)

The 6D distribution $P(R_1,R_2,D_{iso},D_\Delta, \theta, \phi)$ was estimated with a bootstrapping procedure as follows:

1) Arrange the signal S and acquisition variables ($\tau_1$, $\tau_2$, b, $b_\Delta$, $\Theta$, $\Phi$) as N=1024 column vectors.
2) Use random sampling with replacement to create a "bootstrap resample"[33] of the signal vector s from the full set of acquired data points.
3) Create M=500 "components" by selecting random points in the 6D [$\log(R_1),\log(R_2),\log(D_\parallel),\log(D_\perp),\cos(\theta),\phi$] space within the limits
   $-1\leq\log(R_1)\leq 1$, $-0.3\leq\log(R_2)\leq 2.7$, $-11\leq\log(D_\parallel)\leq -8.3$, $-11\leq\log(D_\perp)\leq -8.3$, $-1\leq\cos(\theta)\leq 1$, and $0\leq\phi\leq 2\pi$.
4) Convert $\log(R_1)$, $\log(R_2)$, $\log(D_\parallel)$, $\log(D_\perp)$, and $\cos(\theta)$ to $R_1$, $R_2$, $D_\parallel$, $D_\perp$, and $\theta$.
5) Convert $D_\parallel$ and $D_\perp$ to $D_{iso}$ and $D_\Delta$ with Eqs. (16) and (17).
6) Expand the vectors with M elements ($R_1,R_2,D_{iso},D_\Delta, \theta, \phi$) and N elements ($\tau_1$, $\tau_2$, b, $b_\Delta$, $\Theta$, $\Phi$) into M×N matrices.
7) Calculate the M×N matrix with the kernel K by inserting the ($R_1,R_2,D_{iso},D_\Delta, \theta, \phi$) and ($\tau_1$, $\tau_2$, b, $b_\Delta$, $\Theta$, $\Phi$) matrices into Eq. (22).
8) Solve Eq. (24) for the M=500 column vector p using an NNLS method. (As a non-limiting example the lsqnonneg routine of Matlab R2015[32] may be used[34]).
9) Select the components with non-zero values in the vector p and discard the others.
10) "Mutate" the components from step 9) by multiplying the values of ($R_1,R_2$, $D_\parallel,D_\perp$) with random number between 0.9 and 1.1 and by adding random numbers between −2° and +2° to the angles ($\theta$, $\phi$).
11) Repeat step 3).
12) Replace components from step 11) with the non-zero components from step 9) and the mutated components in step 10).
13) Repeat steps 4)-12) $10^2$ times and store the obtained vector p.
14) Repeat steps 2)-13) $10^3$ times to create a set of $10^3$ vectors p.
15) Select the components with non-zero amplitude in the $10^3$ vectors p.
16) Calculate all possible 1D and 2D projections of $P(R_1,R_2,D_{iso},D_\Delta)$ by Gaussian convolution of the discrete components from step 15) onto 100×100 rectangular grids in the $\log(R_1)$, $\log(R_2)$, $\log(D_{iso})$, and $\log(D_\parallel/D_\perp)$ spaces.
17) Display the 2D and 1D distributions as contour plots and traces.
18) Select components with $D_\parallel/D_\perp > 10$.
19) Calculate the orientation distribution function $P(\theta, \phi)$ by Gaussian convolution of the discrete components from step 19) onto a spherical mesh with $10^3$ nodes.
20) Display the distribution $P(\theta, \phi)$ as a spherical mesh with the radius for each mesh point scaled by the corresponding value of $P(\theta, \phi)$.

Results

FIGS. 3a-b show the acquisition protocol as signal S and values of $\tau_1$, $\tau_2$, b, $b_\Delta$, $\Theta$, and $\Phi$ as a function of acquisition number. Projections of the estimated distribution $P(R_1,R_2,D_{iso},D_\Delta, \theta, \phi)$ are displayed in FIG. 3c. The figure shows 2D projections for each pair of parameters $R_1$, $R_2$, $D_{iso}$, and $D_\parallel/D_\perp$ (contour plots) as well as 1D projections (traces). The signal $S_{fit}$ calculated from the distribution and the residual $(S-S_{fit})$ are plotted in FIG. 3a. The values of $(S-S_{fit})$ indicate a signal-to-noise ratio for data points acquired with $\tau_1=\infty$, $\tau_2=0$, and b=0. Since the studied sample comprises reverse micellar and reverse hexagonal phases, we expect two water components with distinct values of the diffusion anisotropy: one isotropic component from the reverse micelles and one with values of $D_\Delta$ approaching 1. Starting with the 1D projections $P(R_1)$, $P(R_2)$, $P(D_{iso})$, and $P(D_\parallel/D_\perp)$, we note that the two components can only be resolved in the $R_2$- and $D_\parallel/D_\perp$-dimensions, while they are indistinguishable in the $R_1$- and $D_{iso}$-dimensions. The peak widths include contributions from the fit uncertainty, giving rise to slightly different positions of the components for each of the bootstrap resamples. The resolution in $R_2$-dimension makes it possible to detect subtle differences in $D_{iso}$ in the 2D projection $P(R_2,D_{iso})$ and to verify that both components have identical $R_1$ in the 2D projection $P(R_1,R_2)$. The insert in FIG. 3c shows the 2D orientation distribution function (ODF) $P(\theta,\phi)$ for the component with $\log(D_\parallel/D_\perp)>1$ as a spherical mesh with radius scaled by the directionally dependent value of $P(\theta,\phi)$. The function indicates that the crystallites of the reverse hexagonal phase are aligned in the z direction of the laboratory reference frame, which coincides with the main magnetic field.

Description of Embodiments

Figure 4:
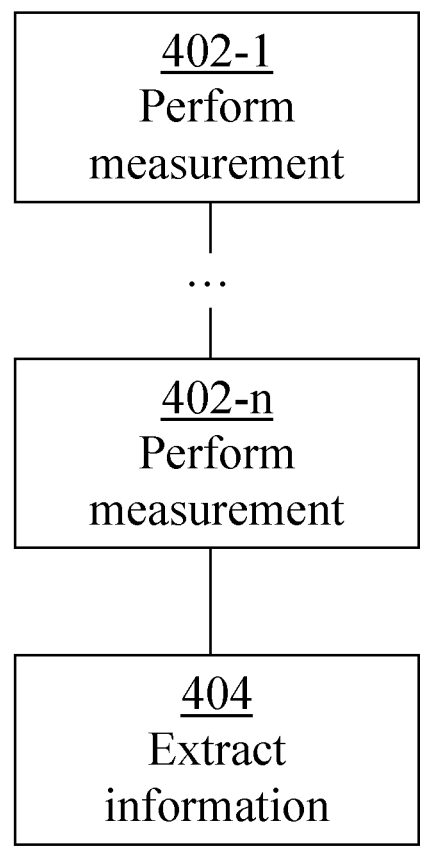
FIG. 4 is a flow chart of a method of extracting information about a sample.

FIG. 4 illustrates a general flow chart of a method of extracting information about a sample. The sample may for example be a biological sample including water, such as brain tissue or biopsy samples of (suspensions) of any organs cell. More generally, the sample includes a nuclear spin system whose properties may be measured by magnetic resonance techniques.

The method may be performed using a state-of-the-art NMR spectrometer or MRI device. As is well-known in the art, such devices may include one or more processors for controlling the operation of the device, inter alia the generation of the magnetic gradient pulse sequences, the acquisition of signals as well as sampling and digitizing the measured signals for forming data representing the acquired signals. The generation of the relaxation encoding sequences and the diffusion encoding magnetic gradient pulse sequences may be implemented using software instructions which may be stored on a computer readable media (e.g. on a non-transitory computer readable storage medium) and be executed by the one or more processors of the device. The software instructions may for example be stored in a program/control section of a memory of the device, to which the one or more processors of the device has access. Collected data representing the measurements may be stored in a data memory of the device, or of a computer or the like which may be connected to the device.

The information extraction and calculations forming part of the method may be performed by a processing device. The operations may be implemented in a set of software instructions which may be stored or embodied on a non-transitory computer readable media and be executed by the processing device. For instance the software instructions may be stored in a program/control section of a memory of the NMR spectrometer/MRI device and executed by the one or more processor units of the spectrometer/device. However it is equally possible to carry out the calculations on a device which is separate from the NMR spectrometer or MRI device, for example on a computer. The device and the computer may for example be arranged to communicate via a communication network such as a LAN/WLAN or via some other serial or parallel communication interface. It should further be noted that, instead of using software instructions, the operation of the method may be implemented in a processing device in the form of dedicated circuitry of the device/computer such as in one or more integrated circuits, in one or more application-specific integrated circuits (ASICs) or field-programmable gate arrays (FPGAs), to name a few examples.

With reference to FIG. 4, the method comprises performing a plurality of magnetic resonance measurements on the sample (step 402-1 through 402-$n$). Each measurement includes subjecting the sample (i.e. the nuclear spin system of the sample) to an encoding sequence or encoding block. At least a part of the encoding sequence of each measurement is adapted to encode a magnetic resonance signal attenuation S due to both nuclear relaxation and diffusion within the sample. The plurality of measurements may be performed in sequence wherein the measurements are performed in turn, one following another.

The encoding sequence of each measurement includes an RF signal sequence encoding a particular relaxation sensitivity in the sample. The encoding sequence of each measurement further includes a gradient pulse sequence providing diffusion encoding in the sample. FIG. 1 discussed earlier illustrates one possible example of an encoding block including an RF signal sequence and a gradient pulse sequence. However, other types of encoding blocks are equally possible.

Generally, both spin echo encodings and stimulated echo encodings may be used. In either case the RF signal sequence may encode for attenuation due to only longitudinal, only transverse relaxation or both longitudinal and transverse relaxation. One example sequence may include a single 90° pulse and a single 180° pulse. The timing of the gradient pulse sequence in relation to the 180° pulse may be varied. For instance the gradient pulse sequence may be performed prior to or subsequent to the 180° pulse. Several such sequences may be repeated before acquisition/detection. Examples of stimulated echo sequences may include a first 90° pulse, a second 90° pulse and a third 90° pulse. The gradient pulse sequence may be performed between the first and the second 90° pulses, and/or subsequent to the third 90° pulse (i.e. before the detection block). These examples sequences are however merely provided as illustrative examples and other sequences are also possible.

Encoding for different levels of signal attenuation due to transverse relaxation and/or longitudinal relaxation may be achieved by varying a relative timing of the RF pulses of the RF signal sequence. For instance, in the example sequence shown in FIG. 1 different attenuation due to transverse relaxation may be achieved by varying $\tau_2$ between at least a subset of the measurements. Different attenuation due to longitudinal relaxation may be achieved by varying $\tau_1$ between at least a subset of the measurements.

Each measurement of the plurality of measurements may include an encoding block providing a respective combination of a relaxation sensitivity encoding and diffusion encoding. The parameters of the encoding block controlling the relaxation sensitivity and diffusion encoding of each measurement may be referred to as a set of acquisition parameters. With reference to FIG. 2, each combination or set may correspond to a particular point in the illustrated acquisition space. Accordingly a first (or $i^{th}$) measurement of the plurality of measurements may include an encoding sequence providing a first (or $i^{th}$) level of signal attenuation due to nuclear relaxation and a first (or $i^{th}$) diffusion encoding. A second (or $(i+1)^{th}$) measurement of the plurality of measurements may include an encoding sequence providing a second (or $(i+1)^{th}$) level of signal attenuation due to nuclear relaxation and a second (or $(i+1)^{th}$) diffusion encoding. The second (or $(i+1)^{th}$) level of signal attenuation due to nuclear relaxation may be different from or equal to the first (or $i^{th}$) level of signal attentution due to nuclear relaxation. The second (or $(i+1)^{th}$) diffusion encoding may be different from or equal to the first (or $i^{th}$) diffusion encoding. Measurements may be acquired in an orderly fashion, e.g. by performing a set of series of measurements wherein, for each series of measurements, one parameter is varied between measurements and the other parameters are held fixed. As disclosed in the above example experiment section it is also possible to perform measurements while randomly selecting parameter combinations within the acquisition space of interest.

At least one of the plurality of measurements includes an encoding block comprising a gradient pulse sequence having a diffusion-encoding tensor representation b with more than one non-zero eigenvalue. The gradient pulse sequence of each one of said at least one of the plurality of measurements include modulated magnetic field gradients in three orthogonal directions. As may be understood from the theory section, this enables isotropic diffusion encoding in the sample (implying a b-tensor with three non-zero and equal eigenvalues) or anisotropic diffusion encoding in the sample in two or more dimensions (i.e. along perpendicular geometrical axes).

The measurements, other than the at least one measurement including a gradient pulse sequence having a diffusion-encoding tensor representation b with more than one non-zero eigenvalue, may include gradient pulse sequences encoding for isotropic diffusion, anisotropic diffusion and/or gradient pulse sequences providing one-dimensional diffusion encoding (i.e. "stick" diffusion encoding sequences). Advantageously, more than one of the plurality of measurements may include gradient pulse sequences which have a respective encoding tensor representation b with more than one non-zero eigenvalue. Thereby different degrees of isotropic diffusion encoding and/or different degrees and/or orientations of anisotropic diffusion encoding may be obtained in the sample for said more than one measurements.

According to the method, at least one parameter of the gradient pulse sequence is varied between at least a subset of the plurality of measurements to provide different diffusion encoding in the sample. For instance, an orientation of the gradient pulse sequence may be varied between measurements to encode diffusion in different directions of the sample. With reference to the above theory and example experiment sections, the at least one parameter of the gradient pulse sequence may include the parameters Θ and/or Φ which may be varied between a subset of the plurality of measurements.

The at least one parameter of the gradient pulse sequence may be varied between measurements to encode for different levels of signal attenuation due to diffusion. For instance a maximum amplitude of the gradient and/or a modulation of the gradient pulse sequence may be varied between measurements. With reference to the above theory and example experiment sections, the at least one parameter of the gradient pulse sequence may include the parameters b and/or $b_A$.

Each measurement 402-1, ..., 402-n may include a detection block (c.f. FIG. 1) wherein echo attenuation signals following the encoding sequence may be recorded. The signal resulting from the plurality of measurements may be recorded as data. The data may be stored for further data processing. The data may for instance be stored in a data memory of the device, or of a computer or the like which may be connected to the device. With reference to the above theory and example experiment sections, the data may be recorded in a signal vector s.

In step 404 of the method, information about the sample is extracted from the signals resulting from the plurality of magnetic resonance measurements 402-1, ..., 402-n. The information extracted in step 404 includes nuclear relaxation and diffusion characteristics for the sample. A probability distribution may be estimated which indicates a probability to find a particular combination of nuclear relaxation characteristics and diffusion characteristics in the sample.

The probability distribution may be estimated based on an equation relating echo signals resulting from said plurality of measurements to a kernel and the probability distribution, wherein the components of the kernel are based on an acquisition parameter and a diffusion or a relaxation characteristic. The equation and the kernel may for instance be given by Equations 11 and 11' presented in the theory section or by equations 21 and 22. The processing device may perform a numeral algorithm for estimating the probability distribution, for instance by performing a numerical inverse integral transform of equation 11 or 21.

The probability distribution provides information about the nuclear relaxation characteristics and diffusion characteristics of the diffusing component(s) of the sample. For instance, a particular combination of nuclear relaxation characteristics and diffusion characteristics may be determined to be present in the sample if the probability distribution indicates a substantial probability for this particular combination (e.g. a probability exceeding a predetermined threshold probability).

Data representing the extracted information (such as the probability distribution and/or a combination/combinations of nuclear relaxation characteristics and diffusion characteristics determined to be present in the sample) may be output by the processing device and stored in the data memory. With reference to the above theory and example experiment sections the nuclear relaxation characteristics may include an estimate of a transverse relaxation rate $R_2$ and/or a longitudinal relaxation rate $R_1$ for each component in the sample.

The diffusion characteristics of the extracted information may include an estimate of an isotropic diffusivity for each component in the sample. The estimate of the isotropic diffusivity may for instance be quantified by the parameter $D_{iso}$ as defined in the theory section.

The diffusion characteristics of the extracted information may include an estimate of an anisotropic diffusivity for each component in the sample. The estimate of the anisotropic diffusivity may for instance be quantified by $D_A$ as defined in equation in the theory section.

The diffusion characteristics of the extracted information may include an estimate of an orientation of a diffusion tensor D representing diffusion for each component in the sample. The orientation may for instance be quantified by $\theta,\phi$ as defined in the theory section.

The diffusion characteristics of the extracted information may include estimates of the elements or components of a diffusion tensor D representing diffusion for each component in the sample. The elements of the diffusion tensor D may include $D_{11}, D_{12}, D_{13}, D_{22}, D_{23}, D_{33}$ as defined in the theory section.

According to the method at least a part of the encoding sequence of each measurement may further be adapted to encode for a phase variation of the magnetic resonance signal due to a flow in the sample. The flow sensitivity may be encoded by controlling the velocity-encoding vector a as defined in equation 7 in the theory section. For instance, the velocity-encoding vector a may be varied between measurements of at least a subset of the plurality of measurements 402-1, ... 402-n. The method may accordingly further comprise extracting information about the flow characteristics.

In the above, the inventive concept has mainly been described with reference to a limited number of examples. However, as is readily appreciated by a person skilled in the art, other examples than the ones disclosed above are equally possible within the scope of the inventive concept, as defined by the appended claims. For instance, the method discussed in connection with FIG. 4 may be performed as an NMR method wherein the measured signals reflect the distribution of characteristics of the sample. The measurements may alternative be performed as part of an MRI method. In that case spatial encoding may be applied to the sample in a manner which per se is known in the art. Signals S may thereby be acquired for each pixel/voxel of the sample and information including the nuclear relaxation and diffusion characteristics discussed above may be extracted on a pixel/voxel basis. The extracted information may accordingly be used to generate contrast in an MRI image.

LIST OF REFERENCES

In the above disclosure, one or more numbers in superscript refer to a correspondingly numbered reference document in the following list of references:

[1] W. S. Price, *NMR studies of translational motion* (Cambridge University Press, Cambridge, 2009).
[2] P. T. Callaghan, *Translational dynamics & magnetic resonance* (Oxford University Press, Oxford, 2011).
[3] K. P. Whittal, and A. L. MacKay, J. Magn. Reson. 84, 134 (1989).
[4] E. O. Stejskal, J. Chem. Phys. 43, 3597 (1965).
[5] R. Blinc et al., Phys. Rev. Lett. 33, 1192 (1974).
[6] P. J. Basser, J. Mattiello, and D. Le Bihan, Biophys. J. 66, 259 (1994).
[7] J. D. Tournier, S. Mori, and A. Leemans, Magn. Reson. Med. 65, 1532 (2011).
[8] S. Mori, and P. C. M. van Zijl, NMR Biomed. 15, 468 (2002).
[9] E. R. Gerstner, and A. G. Sorensen, Semin. Radiat. Oncol. 21, 141 (2011).
[10] A. A. Hofling et al., NMR Biomed. 22, 1100 (2009).
[11] D. G. Cory, A. N. Garroway, and J. B. Miller, Polymer Prepr. 31, 149 (1990).

[12] P. P. Mitra, Phys. Rev. B 51, 15074 (1995).
[13] Y. Cheng, and D. G. Cory, J. Am. Chem. Soc. 121, 7935 (1999).
[14] P. T. Callaghan, and I. Furó, J. Chem. Phys. 120, 4032 (2004).
[15] N. Shemesh et al., NMR Biomed. 23, 757 (2010).
[16] J. Finsterbusch, Annu. Rep. NMR Spectrosc. 72, 225 (2011).
[17] D. Topgaard, Microporous Mesoporous Mater. 205, 48 (2015).
[18] S. Eriksson, S. Lasič, and D. Topgaard, J. Magn. Reson. 226, 13 (2013).
[19] D. Topgaard, Microporous Mesoporous Mater. 178, 60 (2013).
[20] S. Lasič et al., Front. Physics 2, 11 (2014).
[21] J. Sjölund et al., J. Magn. Reson. 261, 157 (2015).
[22] F. Szczepankiewicz et al., Neuroimage 104, 241 (2015).
[23] N. Shemesh et al., Magn. Reson. Med. In press).
[24] S. Eriksson et al., J. Chem. Phys. 142, 104201 (2015).
[25] J. P. de Almeida Martins, and D. Topgaard, Submitted.
[26] J. D. Tournier et al., Neuroimage 23, 1176 (2004).
[27] H. C. Torrey, Phys. Rev. 104, 563 (1956).
[28] C.-F. Westin et al., Med. Image Comput. Comput. Assist. Interv. 8675, 209 (2014).
[29] S. Mori, and P. C. M. van Zijl, Magn. Reson. Med. 33, 41 (1995).
[30] P. J. Basser, and D. K. Jones, NMR Biomed. 15, 456 (2002).
[31] B Jönsson et al., *Surfactants and polymers in aqueous solution* (John Wiley & Sons Ltd, 1998).
[32] (The MathWorks, Natick, Mass., 2015).
[33] B. Efron, Biometrika 68, 589 (1981).
[34] C. L. Lawson and R. J. Hanson, *Solving least squares problems* (Prentice-Hall, Englewood Cliffs, N.J., 1974)

The invention claimed is:

1. A method of extracting information about a sample, the method comprising:
performing a plurality of magnetic resonance measurements on the sample, each measurement including subjecting the sample to an encoding sequence, at least a part of the sequence being adapted to encode a magnetic resonance signal attenuation due to nuclear relaxation and diffusion,
wherein at least one parameter of a gradient pulse sequence is varied between at least a first subset of said plurality of measurements, and at least one measurement of said first subset includes a gradient pulse sequence comprising a diffusion-encoding tensor representation with more than one non-zero eigenvalue,
and wherein at least a second subset of said plurality of measurements include encoding for different levels of magnetic resonance signal attenuation due to nuclear relaxation; and
extracting information about the sample from signals resulting from said plurality of magnetic resonance measurements, the information including nuclear relaxation and diffusion characteristics for the sample,
wherein extracting the information includes estimating a representation of a probability distribution indicating a probability to find a particular combination of nuclear relaxation characteristics and diffusion characteristics in the sample, the combination including: a longitudinal and/or a transverse relaxation rate, and one or more of: an isotropic diffusion, an anisotropic diffusion, and an orientation of a diffusion tensor,
wherein the probability distribution is estimated by determining a solution to an equation relating echo signals resulting from said plurality of measurements to a product of a kernel and the probability distribution, wherein components of the kernel are based on an acquisition parameter and a diffusion or a relaxation characteristic.

2. The method according to claim 1, wherein said at least one parameter of a gradient pulse sequence is varied between measurements to provide different diffusion encoding in the sample.

3. The method according to claim 1, wherein said at least one parameter of a gradient pulse sequence is varied between measurements to encode for different levels of signal attenuation.

4. The method according to claim 1, wherein one or more of a modulation of a gradient pulse sequence, a maximum gradient amplitude, and an orientation of the diffusion encoding are varied between measurements.

5. The method according to claim 1, wherein at least a third subset of the measurements include encoding for different levels of signal attenuation due to transverse relaxation and/or longitudinal relaxation.

6. The method according to claim 1, wherein the nuclear relaxation characteristics of the extracted information includes an estimate of a transverse relaxation rate and/or a longitudinal relaxation rate for the sample.

7. The method according to claim 1, wherein the diffusion characteristics of the extracted information include estimates of the elements of a diffusion tensor representing diffusion for a component in the sample.

8. A method of determining diffusion characteristics of a biological sample including water using magnetic resonance measurements, the method comprising:
performing a plurality of magnetic resonance measurements on the sample, each measurement including subjecting the sample to an encoding sequence, at least a part of the sequence being adapted to encode a magnetic resonance signal attenuation due to nuclear relaxation and diffusion,
varying at least one parameter of a gradient pulse sequence comprising a diffusion-encoding tensor representation with more than one non-zero eigenvalue,
encoding for different levels of magnetic resonance signal attenuation due to nuclear relaxation, and
extracting information including a probability distribution indicating a probability to find a particular combination of nuclear relaxation characteristics and diffusion characteristics in the sample, the combination including: a longitudinal and/or a transverse relaxation rate, and one or more of an isotropic diffusion and an anisotropic diffusion.

9. The method of claim 8, wherein the probability distribution is estimated by determining a solution to an equation relating echo signals resulting from the plurality of measurements to a product of a kernel and the probability distribution, wherein components of the kernel are based on an acquisition parameter and a diffusion or a relaxation characteristic.

10. The method of claim 8, wherein the at least one parameter of a gradient pulse sequence is varied between measurements to provide different diffusion encoding in the sample.

11. The method of claim 8, wherein the at least one parameter of a gradient pulse sequence is varied between measurements to encode for different levels of signal attenuation.

12. The method of claim 8, wherein the measurements include one or more of a modulation of a gradient pulse sequence, a maximum gradient amplitude, and an orientation of the diffusion encoding.

13. The method of claim 8, wherein the measurements include encoding for different levels of signal attenuation due to transverse relaxation or longitudinal relaxation.

14. The method of claim 8, encoding for different levels of signal attenuation due to transverse relaxation and longitudinal relaxation.

15. The method of claim 8, further comprising estimating a transverse relaxation rate and/or a longitudinal relaxation rate for the sample.

16. The method of claim 8, wherein the diffusion characteristics of the extracted information include estimates of the elements of a diffusion tensor representing diffusion for a component in the sample.

* * * * *